US009248240B2

(12) United States Patent
Casey et al.

(10) Patent No.: US 9,248,240 B2
(45) Date of Patent: Feb. 2, 2016

(54) FORMULATION DELIVERY DEVICE

(75) Inventors: William J. Casey, San Diego, CA (US); Tyler J. Holschlag, Carlsbad, CA (US)

(73) Assignees: AstraZeneca Pharmaceuticals LP, Wilmington, DE (US); Amylin Pharmaceuticals, LLC, Wilmington, DE (US)

( * ) Notice: Subject to any disclaimer, the term of this patent is extended or adjusted under 35 U.S.C. 154(b) by 1253 days.

(21) Appl. No.: 12/579,028

(22) Filed: Oct. 14, 2009

(65) Prior Publication Data
US 2010/0094254 A1    Apr. 15, 2010

Related U.S. Application Data

(60) Provisional application No. 61/105,364, filed on Oct. 14, 2008.

(51) Int. Cl.
*A61M 5/32*    (2006.01)
*A61M 5/145*   (2006.01)
*A61M 5/50*    (2006.01)
A61M 5/20      (2006.01)
A61M 5/158     (2006.01)

(52) U.S. Cl.
CPC ............. *A61M 5/32* (2013.01); *A61M 5/1452* (2013.01); *A61M 5/3232* (2013.01); *A61M 5/3287* (2013.01); *A61M 5/504* (2013.01); *A61M 5/5013* (2013.01); *A61M 2005/1585* (2013.01); *A61M 2005/2073* (2013.01); *A61M 2205/8281* (2013.01)

(58) Field of Classification Search
CPC ....... A61M 5/32; A61M 5/322; A61M 5/321; A61M 5/3232; A61M 5/3287; A61M 2005/1587; A61M 5/1452; A61M 5/5013; A61M 5/504; A61M 2005/1585; A61M 2005/14506; A61M 2005/2073; A61M 2205/8281
USPC ............. 604/134–139, 157, 164.12, 63, 158, 604/167.02, 195, 194, 156, 506
See application file for complete search history.

(56) References Cited

U.S. PATENT DOCUMENTS

| 4,755,173 | A | * | 7/1988 | Konopka | ......... A61M 25/0606 128/DIG. 26 |
|---|---|---|---|---|---|
| 4,850,977 | A | | 7/1989 | Bayless | |
| 4,874,382 | A | | 10/1989 | Lindemann et al. | |
| 5,067,942 | A | | 11/1991 | Jaffe et al. | |
| 5,092,853 | A | | 3/1992 | Couvertier, II | |
| 6,626,868 | B1 | * | 9/2003 | Prestidge | ............ A61B 5/1405 604/158 |
| 6,811,545 | B2 | * | 11/2004 | Vaillancourt | ......... A61M 5/321 604/158 |
| 6,926,696 | B2 | | 8/2005 | Mohammed | |

(Continued)

Primary Examiner — Bhisma Mehta
Assistant Examiner — Jenna Zhang
(74) Attorney, Agent, or Firm — Mintz, Levin, Cohn, Ferris, Glovsky and Popeo, P.C.

(57) ABSTRACT

The present invention provides a device for injection of formulations into a patient. In one embodiment the injection is sub-cutaneous. The device is convenient for injecting viscous formulations that would otherwise clog conventional injection devices, for example formulations containing microspheres, suspensions, and other viscous substances. Generally, the device features a needle for piercing the skin, an internal chamber for holding and transmitting fluid, a plunger for applying pressure to the internal chamber, a switch for triggering withdrawal of the needle, a sheath at least partially encompassing the needle and having a flow path within the sheath, and a spring that expands when the switch is triggered, and which thereby at least partially withdraws the needle from the sheath.

17 Claims, 4 Drawing Sheets

(56) References Cited

U.S. PATENT DOCUMENTS

| | | |
|---|---|---|
| 7,001,396 B2 | 2/2006 | Glazier et al. |
| 2004/0158207 A1* | 8/2004 | Hunn .................. A61M 5/158 604/164.01 |
| 2007/0060889 A1* | 3/2007 | Adams ............... A61B 17/3415 604/164.01 |
| 2007/0100284 A1* | 5/2007 | Leinsing ........... A61M 25/0631 604/164.01 |

* cited by examiner

FORMULATION DELIVERY DEVICE

This application claims the benefit of U.S. provisional application Ser. No. 61/105,364 filed Oct. 14, 2008, which is hereby incorporated by reference in its entirety, including all tables, figures, and claims.

BACKGROUND

Hypodermic syringes are used to inject or extract liquid solutions from body tissues. Pain experienced by patients using hypodermic syringes continues to be a problem, and is a primary cause of missed drug administrations and appointments. Smaller gauge needles have been introduced in an effort to reduce pain associated with penetrating skin surfaces with needles. However, smaller gauge needles tend to clog when being used to administer viscous drug solutions or suspensions, including suspensions containing microspheres. Larger gauge needles do not tend to clog when being used to administer drug solutions through the skin, but cause the patient significant additional pain or discomfort when entering the skin.

A variety of devices have been proposed for the subcutaneous administration of drug solutions, formulations, and suspensions. One type of device utilizes a dual-compartment syringe. One compartment of the syringe contains a diluent, and the other compartment contains a powdered drug. The sidewall of the syringe contains a groove just forward of the stopper between the chambers. As the plunger is pushed, the groove allows fluid to leak into the drug chamber. The drug and diluent are mixed by the turbulence created as the fluid from the diluent chamber enters the drug chamber, and then the injection is administered through an attached syringe. The disadvantages of this method include use of a non-custom syringe and a large needle which needs to accommodate the drug/diluent mixture, thereby causing excessive pain in the patient.

Devices which include a sheath wrapped around a syringe needle have also been used. However, to the extent that the sheath may be made of a polymer, the sheath does not dilate an injection area once the needle is inserted into skin. In these devices the sheaths protect the needle during injection and during the withdrawal of the needle after injection. For example, a common application involves a sheath which is tightly wrapped over a steel needle. The needle is inserted into the skin, and once in place, the needle is withdrawn from the skin, leaving the sheath in a desired position within the skin. After this a drug delivery device is used to inject fluid through the sheath. But these devices present difficulties to users who usually must perform injections with only one hand available to manipulate the device.

Thus a need exists for injection devices that allow for the administration of substances of higher viscosity while minimizing patient discomfort.

SUMMARY OF THE INVENTION

The present invention provides a device for injection of formulations into a patient. In one embodiment the injection is sub-cutaneous. The device can be used to inject any formulation, but may find particular utility in injecting viscous formulations that tend to clog conventional injection devices, for example formulations containing microspheres, suspensions, and other viscous substances. In one embodiment the device features a needle for piercing the skin, an internal chamber for holding and transmitting fluid, a plunger for applying pressure to the internal chamber, a switch for triggering withdrawal of the needle, a sheath at least partially encompassing the needle and having a flow path within the sheath, and a spring that expands when the switch is triggered, and which thereby at least partially withdraws the needle from the sheath.

The present invention provides a device for delivering a formulation to a patient, for example by sub-cutaneous delivery. The device is an injection device having a needle with a point on one end to penetrate skin, an internal chamber for holding and transmitting the formulation, and a plunger for applying pressure to the internal chamber. A switch is present exposed to the internal chamber that moves the device from a first position to a second position when pressure within the internal chamber reaches a trigger value. The device has a sheath having proximal and distal ends and at least partially encompasses the needle. A flow path is present within the sheath that connects the internal chamber and the exterior of the device through the distal end of the sheath when the switch is in the second position. The device also has a spring directly or indirectly connected to the needle that expands from a first compressed position to a second expanded position in response to the switch moving to the second position, which action at least partially withdraws the needle from the sheath. In one embodiment the device is configured in a first, piercing position wherein the needle protrudes from the distal end of the sheath and the spring is in a compressed position. The device has a second, retracted position wherein the needle is at least partially retracted within the sheath and the spring is in an expanded position.

In one embodiment the internal chamber is divided by a septum into an upper internal chamber and a lower internal chamber, and the spring is present within the lower internal chamber. The device can be configured in a first, piercing position where the needle protrudes from the distal end of the sheath and the spring (in embodiments where present) is in a compressed position. The device can also be configured in a second, retracted position where the needle is at least partially retracted from the sheath and the spring (in embodiments where present) is in an expanded position. The device can also have the needle present on a needle holder in the lower internal chamber and holds the needle in a first piercing position or a second retracted position. In one embodiment the septum is the upper portion of the needle holder. A flow path connects the internal chamber and the exterior of the device, and a passageway can be present that flows from the upper internal chamber, through the lower internal chamber, and flows through the distal end of the sheath to the exterior of the device. The passageway can also divert through one or more additional pathways after leaving the upper internal chamber and before flowing into the lower internal chamber. In one embodiment the needle is a solid state needle.

In one embodiment of the device, when the switch is in the first position it prevents the device from moving from the first piercing position to the second retracted position. The device can be prevented from moving from the first piercing position to the retracted second position by the physical presence of the switch. The device can move from the first position to the second position by triggering of the switch, which occurs in response to an increase of pressure within the internal chamber. Thus, in one embodiment the switch is a pressure-sensitive switch which changes the device from the first to the second position in response to higher air or fluid pressure within the internal chamber. In this embodiment when the switch moves from the first position to the second position the needle holder is released and the spring expands, allowing the needle to move, and change the device from the first piercing position to the second retracted position. Expansion of the spring causes the needle to at least partially withdraw from the sheath, and thereby open the flow path from the internal chamber through the sheath and out the distal end of the sheath. It is not necessary that the needle withdraw completely from the sheath, only that a flow path is opened allowing the formulation to pass through the sheath. In one embodiment the sheath is tapered. It can be made of any suitable plastic or polymeric material possessing sufficient strength to maintain its form under stresses of use. Non-limiting examples of suitable materials for the sheath include pebax, polyurethane, urethane, teflon and polyethelene.

In another embodiment the device utilizes a component for storage of energy other than a spring. The precise component for storage of energy (an energy store) is not important in the invention, but rather that sufficient energy be stored by the component for at least partial withdrawal of the needle from the sheath, and that such withdrawal be under the control of the user. For example, the device can have a magnetic base situated on or within the device and extending a magnetic field. There can also be present a magnet directly or indirectly associated with the needle and within the magnetic field of the magnetic base. The magnet moves towards the magnetic base when the switch moves from the first position to the second position. The needle moves from a first piercing position to a second retracted position when the magnet moves toward the magnetic base, and the needle at least partially withdraws from the sheath. The internal chamber can also be divided into upper and lower chambers, as described above, and the magnet can be present on the needle holder. The needle holder can be slidably present within the internal chamber.

In another aspect the present invention provides methods for injecting a formulation into a subject, for example by sub-cutaneous delivery. The methods involve penetrating the skin of the subject with the needle of a device as described herein, causing pressure to be applied to the plunger of the device to increase the pressure in the internal chamber of the device, or increasing the pressure within the internal chamber by other means, and thereby injecting the formulation into the subject. Any device described herein can be used in the methods. In one embodiment when the switch is moved from the first position to the second position the spring expands at least partially retracting the needle from the sheath, and the formulation flows on a flow path from the internal chamber and into the subject. In another embodiment when the switch is moved from the first position to the second position the needle retracts completely from the sheath. The switch can be prevented from moving from the first position to the second position because a portion of the switch physically prevents the needle holder from moving the needle from the first piercing position to the second retracted position. In another embodiment of the methods the device used has no switch and no spring, but increasing the pressure in the internal chamber causes a piston to move from a first to a second position, thereby opening a flow path from the internal chamber to the injection pathway.

The devices used in the methods have a retracting mechanism directly or indirectly connected to the needle that moves from a first piercing position to a second retracted position when the switch moves to the second position, and which thereby at least partially withdraws the needle from the sheath. By retracting mechanism is meant those mechanisms for storing and releasing a force to at least partially retract the needle from the sheath. For example, the use of a mechanical spring in the device is a retracting mechanism, as is the use of a magnetic field, or the use of frictional forces. Retracting mechanisms can be used in conjunction with other parts of the device, such as a needle holder, for converting the stored force into needle motion. The retracting mechanism withholds the stored force until the appropriate time, such as when a trigger value of pressure has built within the internal chamber of the device.

In another embodiment of the methods pressure applied to the plunger causes an increase in pressure within the internal chamber and exerts pressure on the switch, which causes the switch to move from the first position to the second position. When the switch moves from the first position to the second position the needle holder moves the needle from the first piercing position to the second retracted position, thus opening a flow path from the upper internal chamber through the lower internal chamber and out of the distal end of the sheath. The pressure applied to the plunger drives the formulation from the internal chamber to the exterior of the device. In some embodiments the spring stores a potential energy when the needle is in the first piercing position, and when the switch moves from the first position to the second position the potential energy of the spring is released and the needle holder moves the needle from the first piercing position to the second retracted position.

In another aspect the invention provides a device for delivering a formulation to a patient, for example by sub-cutaneous delivery. The device has a needle having a point on the distal end to penetrate skin, an internal chamber for holding and transmitting the formulation, a plunger for applying pressure to the internal chamber, a piston slidably located within the internal chamber and having a first and second position within the internal chamber, the piston moving from the first position to the second position when pressure applied by the plunger reaches a threshold pressure. The device also has a sheath having proximal and distal ends and at least partially encompassing the needle and having a flow path within the sheath connecting the internal chamber and the exterior of the device through the distal end of the sheath; when the switch is in the second position, and further contains a passageway located within the piston that connects the internal chamber with the flow path within the sheath when the piston is in the second position, the passageway being closed when the piston is in the first position. In one embodiment, when the threshold pressure is reached the piston overcomes a frictional resistance and moves from the first position to the second position. By "slidably located" is meant that the position of the unit is movable by sliding within the internal chamber. The piston can be held in place by frictional forces, and in some embodiments by a switch or other removable barrier. The piston can be induced to slide within the internal chamber in response to reaching a threshold pressure placed on the piston. The threshold pressure is that amount of pressure that induces the piston to slide within the chamber. In other embodiments the unit that is slidably located can be held in place by mechanical forces and moved by the action of a spring.

In another aspect the invention provides a device for delivering a formulation to a patient, for example by sub-cutaneous delivery. The device has a needle that has a point to penetrate skin, an internal chamber for holding and transmitting the formulation, a plunger for applying pressure to the internal chamber, and a camming piston slidably located within the internal chamber and having a first and second position within the internal chamber. The piston moves from the first position to the second position when pressure applied by the plunger reaches a threshold pressure. A slot having a vertical portion is present in the wall of the internal chamber. The device also has a guiding mechanism connected to the camming piston and positioned in the slot of the wall of the internal chamber. The guiding mechanism slides or travels within the slot in response to pressure within the internal chamber. The device further has a sheath having proximal and distal ends and at least partially encompassing the needle and having a flow path within the sheath connecting the internal chamber and the exterior of the device through the distal end of the sheath when the switch is in the second position. The device further has a spring directly or indirectly connected to the needle that expands from a compressed position to an expanded position causing the device to move from a first piercing position to a second, retracted position when the guiding mechanism moves to the vertical portion of the slot. In one embodiment the needle protrudes from the sheath when the device is in the first, piercing position. In one embodiment the slot of the device also has a substantially horizontal portion. In another embodiment of the device, when the guiding mechanism travels from the substantially horizontal portion of the slot to the vertical portion of the slot, the device moves from a first, piercing position to a second, retracted position, which can cause the needle to at least partially withdraw from the sheath.

DETAILED DESCRIPTION

Figure 1:
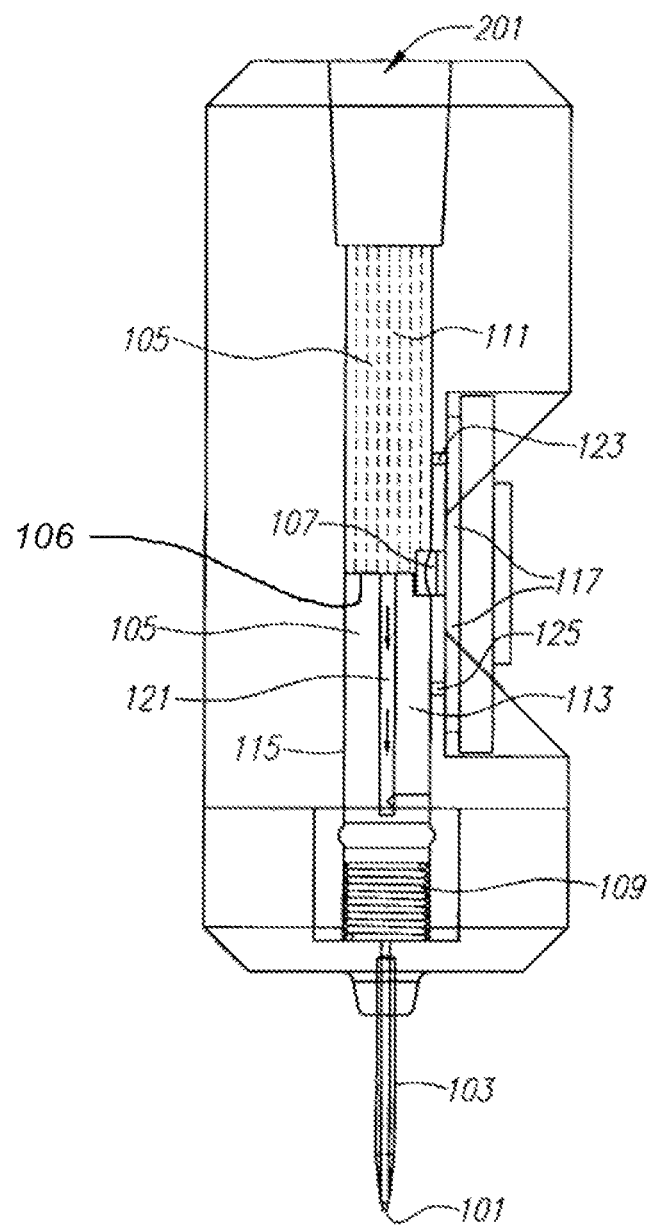
FIG. 1 provides a cross-sectional view of one embodiment of a device of the invention illustrating one design of the device. In this Figure the switch is in the first position and the spring is in the piercing position.

The present invention provides several advantages over previous devices for administration of formulations. Use of a needle with a smaller diameter is most desirable to minimize discomfort to the patient. However, when a formulation is to be injected that has a high viscosity, smaller needles often clog and become unable to deliver such a formulation. The present invention utilizes a needle for its necessary purpose in puncturing the skin in order to create an opening in the skin into which the formulation can be introduced. The invention also provides a sheath surrounding the needle which can hold open the opening in the skin produced by the needle, even after the needle is withdrawn from the sheath. In one embodiment the needle utilized in the invention is a solid state needle, i.e., does not have a hollow interior and is not a hollow needle. In another embodiment fluid does not pass through the center or core of the needle. In yet another embodiment the invention provides a mechanism for at least partially withdrawing the needle within the sheath after its necessary purpose has been achieved in puncturing the skin. In one embodiment the needle completely withdraws from the sheath. After the needle at least partially withdraws within the sheath a viscous formulation can be conveniently injected through the diameter of the sheath and thus administered to the patient through the opening in the skin created by the needle. The sheath can also serve to hold the opening made by the needle open for administration of formulation. Thus, using the same inner diameter less clogging of the injection device occurs and formulations, solutions, and suspension with higher viscosity can be conveniently and safely injected with a minimum of discomfort to the patient. In yet another embodiment the sheath is made of a material that can expand or stretch to allow formulation to pass through.

In one embodiment the device is a unitary device. By "unitary" is meant that to inject formulation no assembly or disassembly of any part of the device is necessary or performed after the user utilizes the device to puncture the skin. For example, a device that would require a user to puncture the skin and then remove the needle manually and attach a syringe is not a unitary device. With a unitary device, the user need only puncture the skin, depress the plunger (or other device part for transmitting force), and thereby inject formulation.

In various embodiments the device is pre-loaded. By "pre-loaded" is meant that the device contains formulation to be injected as it is provided to the user. Thus, with a pre-loaded device the user does not need to load formulation into or through the device. With a pre-loaded device the user need only puncture the skin, depress the plunger (or other part for transmitting force), and thereby inject formulation.

In various embodiments the device can be pre-loaded with any amount of formulation, for example, up to 3000 ul of formulation. The device generally will dispense from about 10 ul to about 1000 ul of formulation, but in various embodiments can be engineered to dispense from about 10 ul to about 50 ul, or from about 10 ul to about 100 ul, or from about 50 ul to about 500 ul, or greater than 1000 ul of formulation.

The formulations to be injected with the device can be any liquid or semi-liquid, or semi-solid formulation. Generally the formulation will have a viscosity of from about 0 centipoise (cP) to about 3000 cP. In a particularly preferred embodiment the formulation has a viscosity of about 30 cP, but in various other embodiments the viscosity of the formulation can be from about 20 cP to about 40 cP, or from about 20 cP to about 50 cP, or from about 20 cP to about 70 cP, or from about 50 cP to about 100 cP. In different embodiments the formulation may contain microspheres, microparticles, nanoparticles. The formulation can also have a syrupy or semi-solid consistency. The formulation can be a solution, a suspension, or any other type of formulation that can be injected with the devices of the invention.

Referring to FIG. 1, a cross sectional illustration of an embodiment of the device is provided, having a needle 101 projecting from the end of the sheath 103. The device of FIG. 1 is depicted with the spring 109 in a compressed position and the device in the first, piercing position, where the pointed end of the needle 101 protrudes from the end of the sheath 103. A plunger (not illustrated) is used to apply pressure to the internal chamber 105 at the top opening 201 of the internal chamber in this embodiment, although various access points can be used. The plunger can be fitted into the top opening 201 of the device. The internal chamber 105 also holds the formulation to be injected. Whether referring to the spring or to the device in the first, piercing position, in this position the needle 101 protrudes through the distal end of the sheath 205 for piercing the skin. In this embodiment the spring is a mechanical spring and holds the energy that will at least partially withdraw the needle from the sheath. With reference to this disclosure persons of ordinary skill will find other methods of storing the energy to be used in retracting the needle when sufficient pressure is applied to the plunger. By the spring being in a "compressed" position is meant that the spring contains sufficient force to move the device from the first, piercing position to the second, retracted position.

A switch 107 is present that is exposed to the internal chamber 105, in the embodiment depicted in FIG. 1 the switch 107 is exposed specifically to the environment of the upper internal chamber 111. When the device is present in the first piercing position the switch 107 prevents the device from moving from the first piercing position (where the needle is available for piercing skin) to the second retracted position. In this example the switch 107 prevents the spring 109 from moving from the first, piercing position to the second, retracted position by the physical presence of the switch blocking movement of the needle holder 115. The internal chamber 105 is divided into an upper internal chamber 111 and a lower internal chamber 113, with the spring 109 in this embodiment being present in the lower internal chamber 113. In this embodiment there is also present a needle holder 115, which holds the needle 101 in the first or second positions. The needle holder 115 can be made of a plastic or other suitable material, and in this embodiment provides the division between the upper and lower chambers in the form of a septum 106 that can be situated on the needle holder. The needle holder can be slidably located within the internal chamber 105. Thus, due to the presence of the septum 106 there is no communication of formulation or air between the upper and lower internal chambers, other than via the side passageway 117 intended for that purpose. FIG. 1 also illustrates the presence of the side passageway 117 that flows from the upper internal chamber 111, to outside the internal chamber through and into the lower internal chamber 113. In one embodiment a bypass 119 is also present to provide a path around the button, if necessary in a particular embodiment. Whether or not the bypass 119 is necessary will depend on the route chosen for the passageway 117 in the specific embodiment. Thus in one embodiment a flow path is traced from the upper internal chamber 111, through the connecting path 123, through the passageway 117, through a bypass 119 (when present), through the second connecting path 125, through the lower internal chamber 113, and exits through the distal end of the sheath. With reference to this disclosure the person of ordinary skill will understand that various designs are possible, some of which can use a side passageway and/or bypass and others in which it will be unnecessary.

Figure 2:
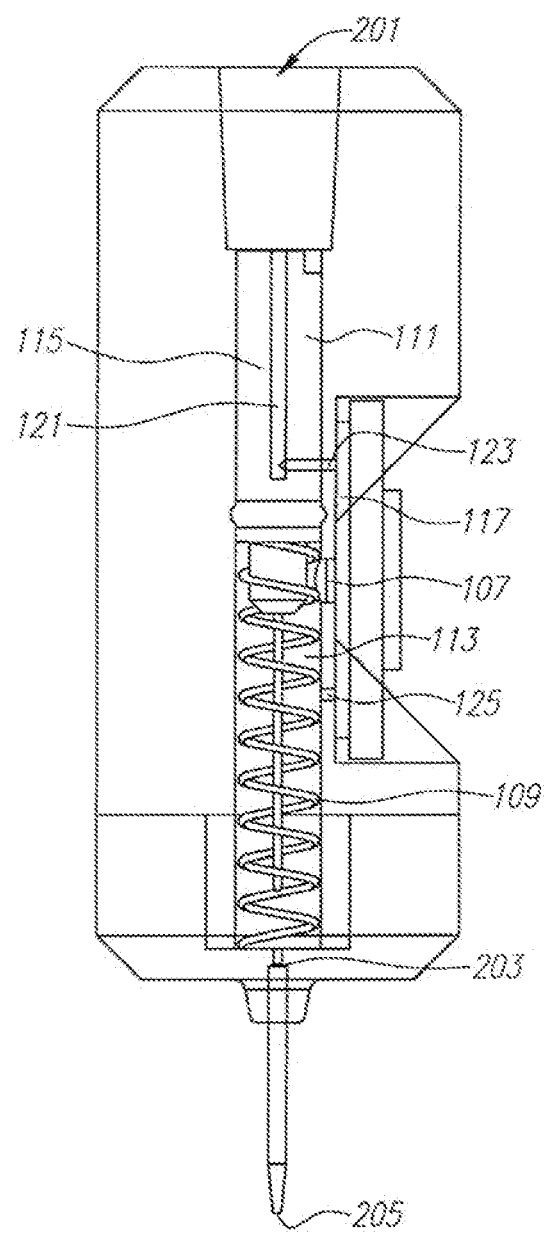
FIG. 2 is a cross-sectional view of one embodiment of the device of the invention, illustrating the relative positions of components of the device in this embodiment. In this Figure the switch is in the second position and the spring is in the retracted position.

Referring to the embodiment depicted in FIG. 2, when a sufficient pressure is built up within the upper internal chamber 111 by application of force to the plunger at the opening of the internal chamber 201, it causes the switch 107 to be displaced from the first position to the second position. The device in FIG. 2 is depicted in the second, retracted position, where the needle 101 has retracted into the sheath 103. When the switch 107 is depressed and moved out of the way of the needle holder 115, the device is moved into the second position and the needle holder 115 is released. The spring 109 is depicted in the expanded position in FIG. 2. Simultaneously, the needle holder 115 rises within the internal chamber, causing the needle 101 to at least partially, or mostly, or entirely withdraw from the sheath 103. This action causes alignment of the passageway within the needle holder 115 and the connecting path 123, thus opening flow to the passageway 117. Thus a flow path is opened, allowing formulation to move from the upper internal chamber 111, through the side passageway 117 and into the lower internal chamber 113 through the second connecting path 125 as pressure is applied to the plunger. From the lower internal chamber 113 the pressure applied by the plunger to the opening of the internal chamber 201 will drive the formulation into the entrance 203 of the sheath and out of the distal end 205 of the sheath, thus administering the formulation to the patient. The sheath can serve not only as a conduit of formulation injected into the patient, but also to hold open the injection site to ensure full administration of formulation. By the spring being in an "expanded" position is meant that the spring released a force that moved the device from the first, piercing position to the second, retracted position. The sheath can be made of a stretchable or expandable material to allow for formulation to pass, whether the needle is completely or only partially or mostly withdrawn from the sheath.

Figure 3A:
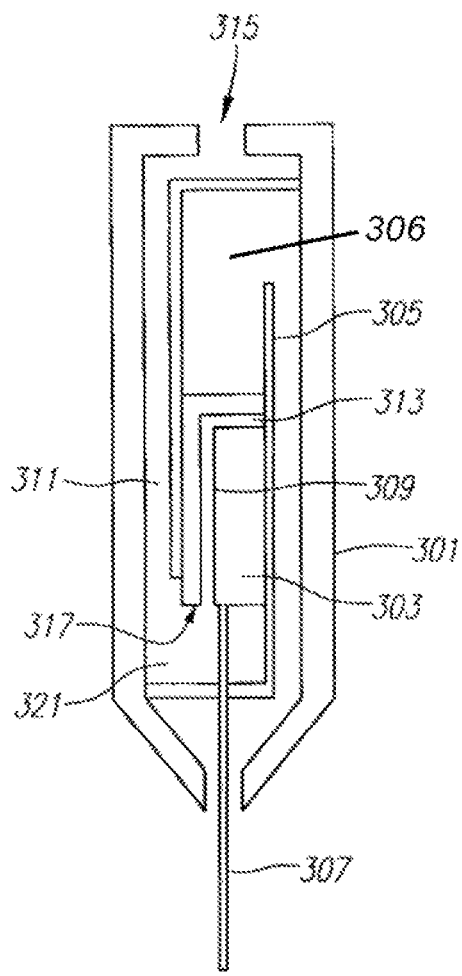
FIG. 3 is a cross-sectional view of one embodiment of a device of the invention, illustrating the relative positions of components of the device. In this embodiment the piston is forced from a first position (3a) to a second position (3b) by pressure applied to the plunger by the user.
Figure 3B:
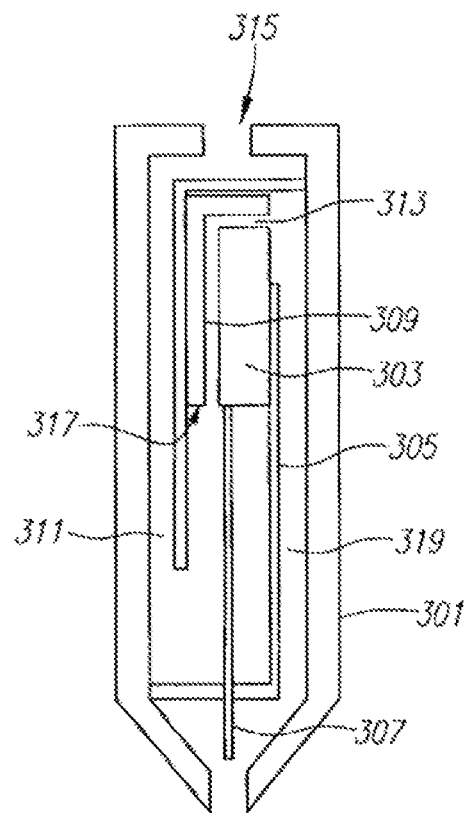

FIG. 3 represents another embodiment of the invention utilizing a piston or spool valve design. Referring to FIG. 3, the body 301 of the device contains an internal chamber 305. A piston 303 is contained within a chamber, dividing the chamber into an upper internal chamber 306 and a lower internal chamber 321. In this embodiment formulation can be initially retained in the lower internal chamber 321. The end 313 of the passageway is closed against the side of the internal chamber 305 when the device is in the first, piercing position. A needle 307 is also attached to the piston 303, and a sheath (not shown, but similar to that depicted in FIGS. 1-2) at least partially encompasses the needle 307. At the top of the device 315 is a space for transmitting pressure to the inside of the device, e.g., via a plunger of a syringe that can be inserted into the space. The pressure is transmitted through a path 311 to be exerted on the bottom of the piston 317, thus exerting an upward pressure on the piston. In this embodiment frictional forces between the piston 303 and the sides of the internal chamber 305 are involved in holding the piston 303 in the first position (FIG. 3a) but with reference to this disclosure persons of ordinary skill in the art will understand additional manners of holding the device in the first position before moving to the second position (FIG. 3b) when sufficient force is applied to the top of the device 315. After puncturing the skin at the site of injection, pressure is applied to the top 315 of the device. When the pressure is sufficient, the piston 303 overcomes the frictional resistance and moves to the second, retracted position (FIG. 3b). A passageway 309 is present within the piston 303 allowing for the flow of formulation when this embodiment of the device is in the second, retracted position. In the second position the end 313 of the passageway is situated so that it opens into the injection pathway 319. Formulation is thus forced through the injection pathway and into the patient. In this device as well the formulation can pass inside the sheath and around the needle 307.

Figure 4A:
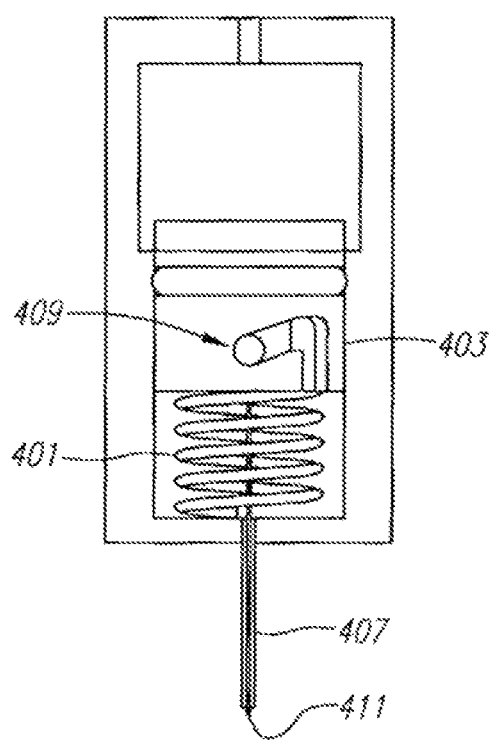
FIG. 4 is a cross-sectional view of one embodiment of a device of the invention that utilizes a camming piston.
Figure 4B:
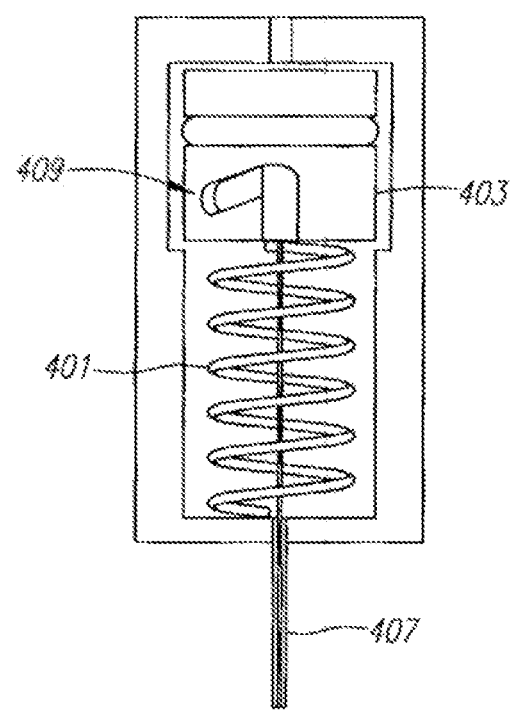

In another embodiment the device features a camming piston contained within an internal chamber, an example of which is depicted in FIG. 4a in the first, piercing position. In this embodiment the spring 401 is connected to a piston 403 that holds the needle 411. The needle 411 is at least partially encompassed by the sheath 407. The piston contains a guiding mechanism 409 that locks into place by fitting into a first slot (not shown) in the inside surface of the cylinder. This first slot can be substantially horizontally configured in the wall of the cylinder. By "substantially horizontal" is meant that the portion of the slot within which the guiding mechanism travels in response to pressure within the internal chamber rises or falls at no greater than a 60 degree angle when the needle of the device is in a fully vertical position. By "horizontal" or "horizontally" configured is meant that the portion of the slot within which the guiding mechanism travels in response to pressure within the internal chamber rises or falls at no greater than a 45 degree angle from fully horizontal when the needle of the device is in a fully vertical position. By "planar" is meant that the portion of the slot within which the guiding mechanism travels in response to pressure within the internal chamber rises or falls at no greater than a 30 degree angle when the needle of the device is in a fully vertical position. A vertical second slot (not shown) is also present in the side of the cylinder connected to the first slot. As pressure is applied to the top of the device, e.g. via a plunger, the piston 403 is moved downward, causing the guiding mechanism 409 to move within the first slot. When the guiding mechanism 409 reaches the second vertical slot, the guiding mechanism 409 is freed to move vertically, and the force contained within the spring 401 is released causing the piston 403 move upward. As the piston 403 moves into the upper portion of its chamber, formulation can pass around its side. Simultaneously the needle 411 is withdrawn from the sheath 407, thus opening up the sheath to the free flow of formulation. Formulation thus passes around the side of the piston 403, through the device and out the sheath surrounding the needle 407, and is thus provided to the patient.

In some embodiments the needle of the device is a solid state needle, which is not hollow, since fluid does not pass through the core of the needle, and the needle in these embodiments is utilized puncture the skin before being withdrawn from the sheath. Any suitable material can be used to manufacture the needle that is capable of forming a needle that can puncture skin (for example, stainless steel, hard plastics, etc).

The body of the device comprising the internal chamber can be made of any suitable material. In one embodiment the body of the device is made of glass, but also could be made of a suitable plastic or other appropriate material known to persons of ordinary skill in the art.

The plunger that is inserted into the opening 201 of the internal chamber can be a plunger from a standard plastic syringe that fits suitably with the device of the invention. The device can be fitted with a Luer-Lok® (Becton Dickinson and Company, Franklin Lakes, N.J.), or other suitable fitting if desired. Thus, the parts of the tools necessary for the user to administer the formulation can conveniently be fitted together and result in a sealed unit.

In a preferred embodiment the devices will be used for delivery of a formulation by sub-cutaneous delivery. But any form of injection can be used with the devices. For example, the devices can be used to deliver formulations by intra-muscular or intra-peritoneal injection, or by any mode of injection.

In one embodiment the switch utilized in the device is a pressure-sensitive switch sized to fit into the internal chamber of the device and having a sensitivity so that when pressure is exerted by the user on the plunger the switch is triggered at the trigger value. The "trigger value" of the switch is that pressure at which the switch is triggered, i.e. forced to move from the first position (where the device is in the first, piercing position) to the second position (where the device is in the second, retracted position). In one embodiment the switch is situated so that it blocks the passageway of the device, and when the switch is triggered and moves into the second position, the passageway is opened and allows for passage of fluid from the upper internal chamber to the lower internal chamber.

In one embodiment the sheath of the device is made of a suitable plastic or polymer material. The sheath can also enter and hold open the opening of the skin created by the piercing action of the needle. After the at least partial or complete withdrawal of the needle from the sheath, the formulation can pass through the center of the sheath and be administered into the patient. The proximal end of the sheath is that portion closest to the body of the device while the distal end is that portion farthest from the body of the device, and the needle protrudes from the distal end when the device is in the first, piercing position. In various embodiments the sheath at least partially encompasses the needle. In one embodiment the sheath substantially encompasses the needle, meaning that that the needle protrudes from the distal end of the sheath by less than 5 mm, or by less than 4 mm, or by less than 3 mm, or by less than 2 mm, or by about 1 mm, or by less than 1 mm.

In other embodiments the device does not feature a spring, but features magnets that are drawn towards each other by magnetic forces. For example, one magnet can be placed on the top of or within the needle holder, and a second magnet can be placed within the lower wall of the upper internal chamber, or for example the upper wall of the lower internal chamber. A magnet can also be placed within a component of the device that divides the upper and lower chambers such as, for example, a septum. Thus, the needle can be present on a needle holder, which is present in the lower internal chamber and holds the needle in the first piercing position. When the switch is triggered in this embodiment the two magnets can be free to move towards each other, and the magnetic attraction pulls the two parts towards one another, thus withdrawing the needle from the sheath. The needle holder then holds the needle in the second retracted position.

The present invention also provides methods of using the device described herein. The methods involve piercing the skin of a patient to receive a formulation, applying pressure to the plunger of the device, and thereby injecting the formulation. The device can be any device described herein. In one embodiment when the switch is moved from the first position to the second position the spring expands and at least partially or completely retracts the needle from the sheath. The formulation then flows on a flow path from the internal chamber and into the subject. In some embodiments when the switch is moved from the first position to the second position the needle retracts completely from the sheath. The device can be designed so that the switch is prevented from moving from the first position to the second position because a portion of the switch physically prevents the needle holder from moving the needle from the first piercing position to the second retracted position. In one embodiment the plunger is inserted into the opening of the internal chamber, and when pressure is applied to the plunger it causes an increase in pressure within the internal chamber, thus exerting a pressure on the switch, such as an internal air or fluid pressure within the chamber. This causes the switch to move from the first position to the second position. In one embodiment when the switch moves from the first position to the second position the needle holder moves the needle from the first piercing position to the second retracted position.

In other embodiments the methods involve piercing the skin with the needle to insert the sheath of the device into the skin, applying pressure to the plunger of the device, causing the device to move from a first, piercing position to a second retracted position, thereby injecting the formulation into the patient.

The device can be designed so that when the needle moves from the first piercing position to the second retracted position a flow path is opened from the upper internal chamber through the lower internal chamber, through the sheath, and out of the distal end of the sheath. The pressure applied to the plunger can drive the formulation from the internal chamber to the exterior of the device. The spring contains a potential energy when the needle is in the first piercing position, and when the switch moves from the first position to the second position the potential energy of the spring is released and the needle holder moves the needle from the first piercing position to the second retracted position.

In other embodiments the device may not have a passageway as depicted in FIGS. 1 and 2. In one example the device can have a membrane, and formulation passes through the membrane when sufficient pressure is applied to the plunger of the device.

The present invention also provides kits containing any device as described herein and instructions for using the device. The instructions can describe how to use the device to inject a formulation into a patient.

Example 1

The performance of an injection device of the invention was evaluated to determine whether lower clogging rates could be achieved with a viscous injectable substance. The embodiment depicted in FIGS. 1-2 was used having a polymer sheath with a nominal inner diameter of 228 um+/−13 um (215-241 um range). For comparison purposes a standard injection needle of size 25 G RW with an inner diameter of 242 um was used.

Criteria for determining that a needle was "clogged" were as follows. A "no clog" injection produced an injection force profile that consisted of an early rising section, a plateau in the middle, and a very short decrease at the end. The maximum force over the entire injection is close to the plateau force. A needle clog is counted when the injection force profile deviates from the no-clog-profile described in 7.4.1. Any peak or spike of force is a deviation, therefore such a force profile is considered as a clog.

For the standard injection needle, 100 injections were performed of 0.95 ml. of a 1 mg/ml microsphere formulation injected into air. The data showed a clog rate of 40% for a conventional glass syringe. For the injection device of the invention, a clog rate of only 18% was realized over 28 injection events performed. Thus, a dramatically lower clog rate was realized despite having a smaller inner diameter than the standard injection needle. Successful injections were realized in more than 82% of injection events for the device of the invention.

The invention claimed is:

1. A device for delivering a formulation to a patient, the device comprising:
    a needle having a point on one end to penetrate skin, wherein the needle is a solid state needle;
    an internal chamber for holding and transmitting the formulation;
    a plunger for applying pressure to the internal chamber;
    a switch exposed to the internal chamber that moves from a first position to a second position when pressure within the internal chamber reaches a trigger value;
    a sheath having proximal and distal ends and at least partially encompassing the needle and having a flow path within the sheath connecting the internal chamber and the exterior of the device when the switch is in the second position; and
    a spring, directly or indirectly connected to the needle, that expands when the switch moves to the second position, and which thereby at least partially withdraws the needle from the sheath,
    wherein the internal chamber comprises an upper internal chamber and a lower internal chamber, and wherein the spring is comprised within the lower internal chamber, wherein the flow path connecting the internal chamber and the exterior of the device comprises a passageway that flows from the upper internal chamber, through the lower internal chamber, and flows through the sheath to the exterior of the device.

2. The device of claim 1 wherein the device is configured in a first, piercing position wherein the needle protrudes from the distal end of the sheath and the spring is in a compressed position.

3. The device of claim 2, wherein, when the switch is in the first position, the switch prevents the device from moving from the first, piercing position to a second, retracted position.

4. The device of claim 3 wherein the device is prevented from moving from the first, piercing position to the second retracted position by the physical presence of the switch.

5. The device of claim 4 wherein the device moves from the first piercing position to the second retracted position in response to triggering of the switch, which occurs in response to an increase of pressure within the internal chamber.

6. The device of claim 3, wherein, when the device moves from the first piercing position to the second retracted position, the spring expands and the needle moves from a compressed position to an expanded position.

7. The device of claim 1 wherein the device is configured in a second, retracted position wherein the needle is retracted from the sheath and the spring is in an expanded position.

8. The device of claim 1 wherein the upper and lower internal chambers are divided by a septum, and the needle is present on a needle holder present in the lower internal chamber.

9. A device for delivering a formulation to a patient, the device comprising:
    a needle having a point on one end to penetrate skin, wherein the needle is a solid state needle;
    an internal chamber for holding and transmitting the formulation;
    a plunger for applying pressure to the internal chamber;
    a switch exposed to the internal chamber that moves from a first position to a second position when pressure within the internal chamber reaches a trigger value;
    a sheath having proximal and distal ends and at least partially encompassing the needle and having a flow path within the sheath connecting the internal chamber and the exterior of the device when the switch is in the second position; and
    a spring, directly or indirectly connected to the needle, that expands when the switch moves to the second position, and which thereby at least partially withdraws the needle from the sheath,
    wherein the internal chamber comprises an upper internal chamber and a lower internal chamber, and wherein the spring is comprised within the lower internal chamber;
    wherein expansion of the spring causes the needle to at least partially withdraw from the sheath, and thereby opens the flow path from the internal chamber through the sheath and out the distal end of the sheath;
    wherein the device is configured in a first, piercing position wherein the needle protrudes from the distal end of the sheath and the spring is in a compressed position;
    wherein, when the switch is in the first position, the switch prevents the device from moving from the first, piercing position to a second, retracted position;
    wherein, when the device moves from the first piercing position to the second retracted position, the spring expands and the needle moves from a compressed position to an expanded position.

10. A method for injecting a formulation into a subject, the method comprising:
penetrating the skin of the subject with a device comprising:
a needle having a point on one end to penetrate skin, wherein the needle is a solid state needle;
an internal chamber for holding and transmitting fluid;
a switch exposed to the internal chamber that moves from a first position to a second position when fluid pressure within the internal chamber reaches a trigger value;
a sheath having proximal and distal ends and at least partially encompassing the needle and having a flow path within the sheath connecting the internal chamber and the exterior of the device when the switch is in the second position;
a retracting mechanism, directly or indirectly connected to the needle, that expands when the switch moves to the second position, and which thereby at least partially withdraws the needle from the sheath, wherein the retracting mechanism is a spring; and
a plunger for applying pressure within the internal chamber;
causing pressure to be applied to the plunger; and
thereby injecting the formulation into the subject, wherein when the switch is moved from the first position to the second position the spring expands at least partially retracting the needle from the sheath, and the formulation flows on a flow path from the internal chamber and into the subject.

11. The method of claim 10 wherein when the switch is moved from the first position to the second position the needle retracts completely from the sheath.

12. A method for injecting a formulation into a subject, the method comprising:
penetrating the skin of the subject with a device comprising:
a needle having a point on one end to penetrate skin, wherein the needle is a solid state needle;
an internal chamber for holding and transmitting fluid;
a switch exposed to the internal chamber that moves from a first position to a second position when fluid pressure within the internal chamber reaches a trigger value;
a sheath having proximal and distal ends and at least partially encompassing the needle and having a flow path within the sheath connecting the internal chamber and the exterior of the device when the switch is in the second position;
a retracting mechanism, directly or indirectly connected to the needle, that expands when the switch moves to the second position, and which thereby at least partially withdraws the needle from the sheath, wherein the retracting mechanism is a spring; and
a plunger for applying pressure within the internal chamber;
causing pressure to be applied to the plunger; and
thereby injecting the formulation into the subject,
wherein the device further comprises a needle holder for holding the needle, and wherein the internal chamber is divided by a septum into an upper internal chamber comprising the switch, and a lower internal chamber comprising the spring;
wherein the causing pressure to be applied to the plunger causes an increase in pressure within the internal chamber and exerts pressure on the switch, which causes the switch to move from the first position to the second position; and
wherein the switch is prevented from moving from the first position to the second position because a portion of the switch physically prevents the needle holder from moving the needle.

13. The method of claim 12 wherein, when the switch moves from the first position to the second position, the needle holder moves the needle.

14. The method of claim 13, wherein the needle protrudes from the distal end of the sheath when the device is configured in a first, piercing position and the needle is retracted from the sheath when the device is configured in a second, retracted position, and wherein, when the device moves from the first, piercing position to the second, retracted position, a flow path is opened from the upper internal chamber through the lower internal chamber and out of the distal end of the sheath.

15. The method of claim 14 wherein the pressure applied to the plunger drives the formulation from the internal chamber to the exterior of the device.

16. The method of claim 12 wherein the spring contains a potential energy when the device is in the first piercing position.

17. The method of claim 16 wherein when the switch moves from the first position to the second position the potential energy of the spring is released and the needle holder moves the needle.

* * * * *